United States Patent [19]

Schirmann

[11] 4,330,485

[45] May 18, 1982

[54] PREPARATION OF PERCARBOXYLIC ACIDS

[75] Inventor: Jean-Pierre Schirmann, Oullins, France

[73] Assignee: PCUK Produits Chimiques Ugine Kuhlmann, Courbevoie, France

[21] Appl. No.: 162,936

[22] Filed: Jun. 25, 1980

[30] Foreign Application Priority Data

Jul. 9, 1979 [FR] France .................... 79 17720

[51] Int. Cl.$^3$ ............................ C07C 179/10
[52] U.S. Cl. ................................ 260/502 R
[58] Field of Search ...................... 260/502 R

[56] References Cited

U.S. PATENT DOCUMENTS

| | | | |
|---|---|---|---|
| 2,814,641 | 11/1957 | Phillips et al. | 260/502 R |
| 2,877,266 | 3/1959 | Korach | 260/502 R |
| 3,169,986 | 2/1965 | Webb et al. | 260/502 R |
| 3,264,346 | 8/1966 | Weiberg | 260/502 |
| 3,284,491 | 11/1966 | Korach et al. | 260/502 R |

Primary Examiner—Werren B. Lone
Attorney, Agent, or Firm—Pennie & Edmonds

[57] ABSTRACT

Process for preparation of percarboxylic acids by the reaction of hydrogen peroxide and a water-miscible carboxylic acid, in the presence of a solvent capable of forming a heteroazeotrope with water, and in the presence of a metalloid oxide catalyst.

9 Claims, No Drawings

PREPARATION OF PERCARBOXYLIC ACIDS

TECHNICAL FIELD

The present invention concerns a procedure for preparation of percarboxylic acids which are particularly useful for selective oxidation of organic compounds.

BACKGROUND ART

Since the work of Ans et al. (Ber. 45, 1845, 1912), it has been known that hydrogen peroxide reacts with aliphatic carboxylic acids to form percarboxylic acids according to a reversible reaction:

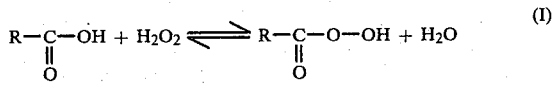

Given the instability of the peroxyacids, this reaction is usually performed at a low temperature. Under these conditions, the state of equilibrium is attained only after several hours of reaction, and this reaction time is prohibitive for an industrial procedure. Thus, it is necessary to use a catalyst. Only one type of catalyst has been proposed up until now: strong mineral acids, such as sulfuric acid, methanesulfonic acid, the arylsulfonic acids, phosphoric acid, the acid phosphoric esters, trifluoroacetic acid, as well as acid cation resins such as Dowex 50 and Amberlite IR-120.

This catalytic process has given rise to numerous studies (D. Swern, ORGANIC PEROXIDES, Wiley Interscience, 1970, Vol. 1, pages 313-369, and pages 428-439), from which it is clearly apparent that the first stage of the reaction is the protonation of the acid function, involving the formation of an oxonium structure capable of reacting with $H_2O_2$, leading, after dehydration, to percarboxylic acid, as per the model:

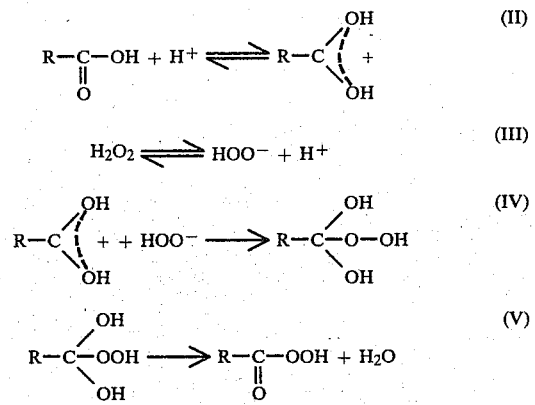

Hydrogen peroxide is most often used in the form of commercial aqueous solutions containing 30-70% water. Moreover, the reaction also produces water, and the state of equilibrium is thus attained well before the hydrogen peroxide is fully transformed. Under these conditions, the product of the reaction is in effect a mixture of acid, hydrogen peroxide, per-acid, water, and strong acid. Because of this, the use of such a mixture as a means of oxidation in organic chemistry produces rather average yields.

To overcome this drawback, it has been proposed that the operation take place in the presence of a heavy excess of carboxylic acid, so as to shift equilibrium toward the right. In this way, by using 10 moles of acetic acid to one mole of hydrogen peroxide, one may obtain a conversion rate of 90% of the hydrogen peroxide into peracetic acid. Use of such an excess allows one to obtain only very diluted solutions of per-acid, and often involves losses in yields due to side reactions, without including the problems of subsequent separation of the products of the reaction.

The proposal has also been made, such as in U.S. Pat. Nos. 2,877,266 and 2,814,641, to operate only with a very slight excess of carboxylic acid, but to operate in the presence of a strong mineral acid and an azeotropic entrainer, in order to eliminate the water and thus shift the equilibrium (I) to the right. Such a practice is in fact excellent in terms of yield of percarboxylic acid in comparison to the hydrogen peroxide used. Compared with the preceding techniques, one could expect that this technique produces high yields in oxidation reactions in organic chemistry. This is scarcely the case, and the yield may be even worse, since the strong-acid catalyst very often gives rise to side reactions. For example, it is well known that, in reactions of epoxidation of olefins by per-acids, the epoxide formed is easily opened and transformed into a mono- or di-ester under the effect of strong-acid catalysts.

It is true that the strong acid may be advantageously neutralized, but then the corresponding salt is generally insoluble in the medium and poses separation problems which are not insignificant on the practical level. Sometimes, the salt is even as good a catalyst of side reactions as the acid itself.

This is why a method has been proposed recently, as in French Pat. Nos. 2,359,132 and 2,300,085, for preparation of organic solutions of percarboxylic acids in two stages, which consists of causing hydrogen peroxide (20-35% solution) to react with propionic acid in an aqueous solution containing 10-45% sulfuric acid, and then extracting the perpropionic acid with the aid of a solvent, such as benzene or dichloropropane. The aqueous phase must be concentrated in order to eliminate the water contributed by the $H_2O_2$ solution and by the reaction. The organic phase is washed in order to eliminate $H_2SO_4$, then dried by, for example, azeotropic distillation. This solution makes it possible in effect to obtain an organic solution of perpropionic acid that is anhydrous and free of sulfuric acid. However, this is a technique which is difficult to put into practice, and consequently costly.

DISCLOSURE OF THE INVENTION

The applicant has discovered that it is possible to arrive at the same result, that is, obtain an anhydrous organic solution of percarboxylic acid untouched by any traces of strong mineral acid, by causing the carboxylic acid and the hydrogen peroxide to react in the presence of new catalysts constituted of a metalloid oxide and an azeotropic entrainer, so as to constantly eliminate from the reaction medium the water contributed by the aqueous solution of hydrogen peroxide, as well as the water resulting from the reaction.

The metalloid oxides which fall within the scope of the present invention are those of selenium, tellurium, arsenic, antimony, bismuth, and boron. By way of non-restrictive examples, one may cite the following oxides: $SeO_2$, $TeO_2$, $As_2O_3$, $As_2O_5$, $Sb_2O_5$, $Bi_2O_3$, and $B_2O_3$.

The carboxylic acids concerned in the invention are the water-soluble aliphatic carboxylic acids, such as formic, acetic, propionic, butyric acids.

The azeotropic entrainer may be chosen advantageously from among the solvents having a boiling point lower than 100° C. and forming a heteroazeotrope with water. By way of non-restrictive examples, one may cite the chlorinated solvents such as chloroform, carbon tetrachloride, methylene chloride, dichloro-1,2-ethane, dichloropropane, hydrocarbon solvents such as cyclohexane, benzene, toluene, esters such as the formates, acetates, propionates, butyrates, isobutyrates of methyl, ethyl, propyl, isopropyl, and n-butyl.

Hydrogen peroxide may be used either in anhydrous form or in the form of commercial aqueous solution assaying from 30 to 70% by weight.

The procedure according to the invention thus comprises placing in contact the carboxylic acid, the azeotropic entrainer, the catalyst, and the hydrogen peroxide, and constantly eliminating water from the reaction medium by azeotropic distillation.

The temperature at which the reaction is performed falls between 40° C. and 100° C., preferably from 40° C. to 70° C. Depending on the temperature chosen and the reaction system used, the elimination of water may be accomplished by operating at atmospheric pressure or at a low pressure. The pressure may thus vary from 20 mm mercury to 760 mm mercury.

The duration of the reaction depends on the nature of the catalyst, the nature of the carboxylic acid, and the nature of the azeotropic entrainer, and the temperature chosen. It may last from several minutes to several hours. The reagents may be used in equimolecular quantities, but a molar deficiency or excess of one of the reagents may also be used. As an illustration, one may use 0.1 to 10 moles of carboxylic acid per mole of hydrogen peroxide but it is preferable to use from 1 to 5 moles.

The catalyst is used at the rate of 0.001 to 0.1 mole of metalloid oxide per mole of hydrogen peroxide. However, a molar ratio from 0.001 to 0.01 mole per mole of hydrogen peroxide used is preferred.

The amount of azeotropic entrainer solvent falls between 50 and 75% by weight of the reaction mixture, so that one may regulate as desired the boiling point of the mixture and effectively eliminate the water.

The reagents may be used in their usual commercial form. The hydrogen peroxide in particular may be used in the form of commercial aqueous solutions assaying from 30 to 70% by weight. It may be advantageous to add to the reaction mixture a hydrogen-peroxide stabilizing product, such as polyphosphates, derivatives of ethylenediaminetetraacetic acid (EDTA), etc.

The percarboxylic acid solution thus obtained may then be used to bring about oxidation of a large number of organic compounds, such as olefins, ketones, amines, aromatic compounds, sulfur-containing derivatives, etc., through a second operation. However, it is not always necessary to resort to that procedure, and the two operations may sometimes be accomplished advantageously at the same time, that is, synthesis of the peracid and its immediate consumption by the molecule to be oxidated. This is a variant of the procedure according to the invention. In this way, when the organic compound one wishes to oxidize with percarboxylic acid forms a heteroazeotrope with water, it may be used as azeotropic entrainer and at the same time react with the percarboxylic acid as the latter is formed. By way of example, one may cite the epoxidation of cyclohexene or allyl chloride by peracetic acid or perpropionic acid. Such a procedure is quite simple to bring about and is particularly safe, since it allows avoidance of any accumulation of peracid in the reaction medium.

Within the scope of that variant, if the compound to be oxidized does not form a heteroazeotrope with water, it is of course quite possible to operate in the presence of an azeotropic entrainer solvent.

BEST MODES FOR CARRYING OUT THE INVENTION

The following examples illustrate in non-restrictive manner the present invention.

EXAMPLES 1 TO 9

In a 250 cm$^3$ reactor equipped with a distillation column having 5 Oldershaw plates, topped by a reflux condenser, place 50 g propionic acid, 70 g azeotropic entrainer solvent, 0.2 g catalyst. This mixture is brought to refulx, then one introduces gradually 0.1 mole of hydrogen peroxide in the form of an aqueous solution, 70% by weight. The condenser is designed so that only the condensed organic phase is returned to the column, the decanted aqueous phase being withdrawn in a continuous manner. The reaction conditions and the results are set forth in the following table.

| EXAMPLE | CATALYST | SOLVENT | T °C. | PRESSURE mm Hg | DURATION mn | $H_2O_2$ REMAINING m mole | PERACID FORMED m mole | $H_2O_2$ DISTILLED |
|---|---|---|---|---|---|---|---|---|
| 1 | — | Cyclohexane | 93° | 760 | 30 | 14.1 | 13 | 34.3 |
| 2 | $As_2O_5$ | Benzene | 94° | 760 | 60 | 2 | 20 | 20 |
| 3 | " | Dichlorethane | 94° | 760 | 60 | 19 | 58 | 11 |
| 4 | $B_2O_3$ | Cyclohexane | 88° | 760 | 30 | 3 | 49.5 | 20.5 |
| 5 | " | Dichlorethane | 94° | 760 | 30 | 6 | 74 | 7 |
| 6 | " | " | 70° | 350 | 60 | 4 | 80 | 4 |
| 7 | " | " | 50° | 150 | 60 | 27 | 62.5 | 15 |
| 8 | $SeO_2$ | " | 94° | 760 | 30 | 3 | 36 | 6 |
| 9 | $Sb_2O_5$ | " | 95° | 760 | 60 | 20 | 65 | 22 |

EXAMPLE 10

In a 500 cm$^3$ reactor equipped with a distillation column having 10 Oldershaw plates, topped by a reflux condenser of the same type as the one described above, place 125 g propionic acid, 175 g dichloro-1,2 ethane, 0.5 g boron oxide $B_2O_3$, and 0.1 g disodium phosphate. Bring to reflux at a pressure of 150 mm Hg. The temperature of the reaction medium is 50° C. Add gradually 0.3 mole of hydrogen peroxide in the form of aqueous solution, 70% by weight. After two hours of reaction during which the water is eliminated in continuous manner by azeotropic distillation, one determines in the medium 0.24 mole perpropionic acid, as well as 0.027 mole hydrogen peroxide, while the distilled aqueous phase contains 0.032 mole hydrogen peroxide.

EXAMPLE 11

The same experiment is repeated as in Example 7, replacing the propionic acid with acetic acid. After 60 minutes of reaction, one determines in the reaction medium 0.07 mole peracetic acid and 0.026 mole of hydrogen peroxide; 0.004 mole hydrogen peroxide has passed to the aqueous phase of the distillate.

EXAMPLE 12

120 g of perpropionic acid solution, prepared according to Example 10, and containing 0.09 mole peracid, is reacted with 8.2 g of cyclohexene, at room temperature. After one hour of reaction, one determines, by gas chromatography, 0.08 mole cyclohexene epoxide.

EXAMPLE 13

In a reactor such as described in Example 1, place 50 g propionic acid, 50 g allyl chloride, as well as 0.1 g arsenic oxide $As_2O_5$. Bring to reflux and adjust the temperature of the reaction medium to 64° C. In 15 minutes, add 0.053 mole hydrogen peroxide in the form of 70% aqueous solution, and eliminate continuously the water contributed by $H_2O_2$, and that formed during the reaction. After one hour of reaction, one determines in the reaction medium 0.034 mole epichlorohydrin, 0.008 mole perpropionic acid, and 0.006 mole hydrogen peroxide. The distillate contains 0.004 mole hydrogen peroxide.

EXAMPLE 14

In a tubular reactor, 15 m long and 2 mm diameter, introduce continuously and simultaneously, after passage through a mixer, 100 g/hr perpropionic acid solution prepared according to Example 10, assaying 6.6% per-acid, and 0.25% hydrogen peroxide, as well as 21 g/hr propylene. The reactor temperature is kept at 50° C. Pressure in the reactor is 8 bars. At the outlet of the reactor, the reaction mixture is decompressed in a continuous process. The gaseous phase is washed with water in a washing column to recover the propylene oxide entrained. The liquid phase is cooled. Analysis of the products of the reaction reveals that 0.011 mole per hour of perpropionic acid leaves the reactor, and that 4 g/hr propylene oxide is formed.

I claim:

1. A process for the preparation of percarboxylic acid which comprises reacting hydrogen peroxide and a water-miscible saturated aliphatic carboxylic acid at a temperature between about 40° and 100° C., in the presence of a selenium oxide, tellurium oxide, arsenic oxide, antimony oxide, bismuth oxide or boron oxide catalyst, and used at the ratio of between about 0.001 to 0.1 mole per mole of hydrogen peroxide, and in the presence of an organic solvent boiling below about 100° C. and continuously eliminating the water by azeotropic distillation contributed by the reactants and that formed during the reaction, said organic solvent being used in an amount falling between about 50 and 75% by weight of the reaction mixture.

2. The process according to claim 1 in which a chlorinated solvent is used as azeotropic entrainer.

3. The process according to claim 1 in which benzene is used as azeotropic entrainer.

4. The process according to claims 1, 2 or 3 in which the carboxylic acid is acetic acid.

5. The process according to claims 1, 2 or 3 in which the carboxylic acid is propionic acid.

6. A process according to claim 1 in which one uses as the azeotropic entrainer an organic compound capable of forming a heteroazeotrope with water and of oxidation with the percarboxylic acid as it is formed in the reaction medium, and oxidizing the organic compound with the percarboxylic acid as it is formed.

7. The process according to claim 6 in which the azeotropic entrainer is an olefin.

8. The process according to claim 7 in which the azeotropic entrainer is cyclohexene.

9. The process according to claim 7 in which the azeotropic entrainer is allyl chloride.

* * * * *